United States Patent
Bohlmann et al.

(10) Patent No.: US 7,846,917 B2
(45) Date of Patent: Dec. 7, 2010

(54) 18-METHYL-19-NORANDROST-4-ENE 17, 17-SPIRO ETHER (18-METHYL-19-NOR-20-SPIROX-4-EN-3-ONE), AND PHARMACEUTICAL PRODUCTS COMPRISING THE SAME

(75) Inventors: Rolf Bohlmann, Berlin (DE); Joachim Kuhnke, Potsdam (DE); Jan Huebner, Berlin (DE); Norbert Gallus, Berlin (DE); Frederik Menges, Glienicke/Nordbahn (DE); Steffen Borden, Berlin (DE); Hans-Peter Muhn, Berlin (DE); Katja Prelle, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 652 days.

(21) Appl. No.: 11/769,952

(22) Filed: Jun. 28, 2007

(65) Prior Publication Data
US 2008/0153787 A1 Jun. 26, 2008

(30) Foreign Application Priority Data
Jun. 29, 2006 (DE) .................. 10 2006 030 416

(51) Int. Cl.
*A61K 31/58* (2006.01)
*C07J 21/00* (2006.01)
(52) U.S. Cl. ........................ 514/173; 540/41
(58) Field of Classification Search ............ 540/41; 514/173
See application file for complete search history.

(56) References Cited

U.S. PATENT DOCUMENTS

| 3,798,213 | A | 3/1974 | Arth et al. |
| 4,584,288 | A | 4/1986 | Nickish et al. |
| 6,787,531 | B1 | 9/2004 | Hilman et al. |
| 2006/0252737 | A1 | 11/2006 | Bohlmann et al. |

FOREIGN PATENT DOCUMENTS

| DE | 3111950 A1 | 9/1982 |
| EP | 1148061 A2 | 10/2001 |
| EP | 1148061 A3 | 10/2001 |

OTHER PUBLICATIONS

K. Nickisch, et al.; "Aldosterone antagonists. 4. Synthesis and activities . . ."; Journal of Medicinal Chemistry; 1991; pp. 2464-2468; vol. 34, No. 8; American Chemical Society; Washington, D.C.
J. Casals-Stenzel, et al.; "The renal action of spirorenone and other . . ."; Arzneim-Forsch; 1984; pp. 241-246; vol. 34, No. 3.

*Primary Examiner*—Barbara P Badio
(74) *Attorney, Agent, or Firm*—Millen, White, Zelano & Branigan, P.C.

(57) ABSTRACT

The present invention describes the novel 18-methyl-19-norandrost-4-ene 17,17-spiro ethers of the general formula I

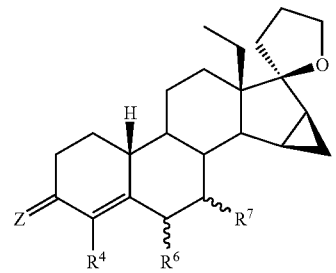

Formel I in which
Z is an oxygen atom, two hydrogen atoms, a group =NOR or =NNHSO$_2$R, where R is a hydrogen atom or a straight- or branched-chain alkyl group having 1 to 4 or 3 to 4 carbon atoms,
$R^4$ is a hydrogen atom, a halogen atom or a trifluoromethyl group,
and $R^6$ and/or $R^7$ may have α or β configuration, and $R^6$ and $R^7$ are independently of one another a hydrogen atom or a straight- or branched-chain alkyl group having 1 to 4 or 3 to 4 carbon atoms or a straight- or branched-chain alkenyl group having 2 to 4 or 3 to 4 carbon atoms or a saturated cycloalkyl group having 3 to 5 carbon atoms or together are a methylene group or a double bond.

The novel compounds have progestational and antimineralocorticoid activity.

20 Claims, No Drawings

18-METHYL-19-NORANDROST-4-ENE 17, 17-SPIRO ETHER (18-METHYL-19-NOR-20-SPIROX-4-EN-3-ONE), AND PHARMACEUTICAL PRODUCTS COMPRISING THE SAME

The present invention relates to 18-methyl-15β,16β-methylene-19-nor-20-spirox-4-en-3-ones [correspond to [(17S)-spiro[18a-homo-15α,16α-dihydro-3'H-cyclopropa-[15,16]estr-4-ene-17,2'-perhydrofuran]-3-ones] of the general formula I

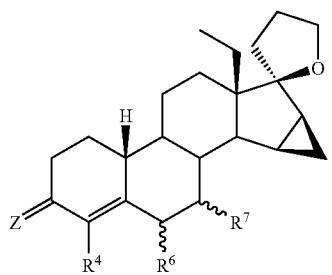

Formel I in which

Z is an oxygen atom, two hydrogen atoms, a group =NOR or =NNHSO$_2$R, where R is a hydrogen atom or a straight- or branched-chain alkyl group having 1 to 4 or 3 to 4 carbon atoms, R$^4$ is a hydrogen atom, a halogen atom or a trifluoromethyl group, and R$^6$ and/or R$^7$ may have α or β configuration, and R$^6$ and R$^7$ are independently of one another a hydrogen atom or a straight- or branched-chain alkyl group having 1 to 4 or 3 to 4 carbon atoms or a straight- or branched-chain alkenyl group having 2 to 4 or 3 to 4 carbon atoms or a saturated cycloalkyl group having 3 to 5 carbon atoms or together are a methylene group or a double bond.

Z is preferably an oxygen atom.

In the case where Z is a group =NOR or =NNHSO$_2$R, R is preferably a hydrogen atom.

A suitable straight- or branched-chain alkyl group having 1 to 4 or 3 to 4 carbon atoms is a methyl, ethyl, n-propyl or an n-butyl group or an isopropyl, iso- or tert-butyl group.

In the case where R$^6$ and/or R$^7$ is a saturated cycloalkyl group, a suitable one therefor is a cyclopropyl, -butyl or -pentyl group.

R$^4$ is preferably a hydrogen atom, a methyl group or a chlorine atom.

A suitable halogen atom R$^4$ is a fluorine, chlorine, bromine or iodine atom;

chlorine is preferred amongst these.

In the case where R$^6$ and/or R$^7$ is a straight- or branched-chain alkyl group having 1 to 4 or 3 to 4 carbon atoms, a suitable one therefor is a methyl, ethyl, n-propyl or an n-butyl group, or an isopropyl, iso- or tert-butyl group. R$^6$ and R$^7$ are preferably a hydrogen atom and a methyl, ethyl or propyl group or together are a methylene group or a double bond. In the case of an alkenyl radical R$^6$ and/or R$^7$, this is in particular an ethenyl radical. The preferred representative of a saturated cycloalkyl group R$^6$ and/or R$^7$ having 3 to 5 carbon atoms is the cyclopropyl radical.

The compounds mentioned below are particularly preferred according to the invention:

18-methyl-15β,16β-methylene-19-nor-20-spiroxa-4,6-dien-3-one
18-methyl-15β,16β-methylene-19-nor-20-spirox-4-en-3-one
18-methyl-6β,7β,15β,16β-dimethylene-19-nor-20-spirox-4-en-3-one
18-methyl-6α,7α,15β,16β-dimethylene-19-nor-20-spirox-4-en-3-one
18-methyl-15β,16β-methylene-7α-propyl-19-nor-20-spirox-4-en-3-one
18-methyl-15β,16β-methylene-7β-propyl-19-nor-20-spirox-4-en-3-one
7α,18-dimethyl-15β,16β-methylene-19-nor-20-spirox-4-en-3-one
7β,18-dimethyl-15β,16β-methylene-19-nor-20-spirox-4-en-3-one
7α-ethyl-18-methyl-15β,16β-methylene-19-nor-20-spirox-4-en-3-one
7β-ethyl-18-methyl-15β,16β-methylene-19-nor-20-spirox-4-en-3-one
7α-ethenyl-18-methyl-15β,16β-methylene-19-nor-20-spirox-4-en-3-one
7β-ethenyl-18-methyl-15β,16β-methylene-19-nor-20-spirox-4-en-3-one
7α-cyclopropyl-18-methyl-15β,16β-methylene-19-nor-20-spirox-4-en-3-one
7β-cyclopropyl-18-methyl-15β,16β-methylene-19-nor-20-spirox-4-en-3-one
4,18-dimethyl-15β,16β-methylene-19-nor-20-spirox-4-en-3-one
4-chloro-18-methyl-15β,16β-methylene-19-nor-20-spirox-4-en-3-one
4,18-dimethyl-6β,7β,15β,16β-dimethylene-19-nor-20-spirox-4-en-3-one
4,18-dimethyl-6α,7α,15β,16β-dimethylene-19-nor-20-spirox-4-en-3-one
4-chloro-18-methyl-6β,7β,15β,16β-dimethylene-19-nor-20-spirox-4-en-3-one
4-chloro-18-methyl-6α,7α,15β,16β-dimethylene-19-nor-20-spirox-4-en-3-one.

Drospirenone (6β,7β-15β,16β-dimethylene-3-oxo-17-pregn-4-ene-21,17β-carbolactone) is a novel progestogen which is present for example in the oral contraceptive YASMIN® and the product ANGELIQ® for the treatment of postmenopausal symptoms (both SCHERING AG). Because of its comparatively low affinity for the progestogen receptor and its comparatively high ovulation-inhibitory dose,

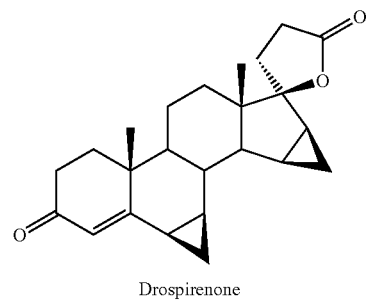

Drospirenone drospirenone is present in YASMIN® in the relatively high daily dose of 3 mg. Drospirenone is notable for having, in addition to the progestational effect, an aldosterone-antagonistic (antimineralocorticoid) and antiandrogenic effect.

Both these properties make drospirenone very similar in its pharmacological profile to the natural progestogen progesterone which, unlike drospirenone however, has insufficient oral bioavailability.

It is therefore an object of the present invention to provide compounds which have a less dissociated profile than drospirenone in relation to their binding to the progesterone receptor and mineralocorticoid receptor, and preferably have a stronger binding than drospirenone to the progesterone receptor. It is preferably intended that the novel compounds have a more potent progestational effect than drospirenone, but have a weaker antimineralocorticoid effect than drospirenone, or one comparable to the latter.

This object is achieved by the provision of the 18-methyl-15β,16β-methylene-19-nor-20-spirox-4-en-3-ones of the general formula I described herein. The novel compounds are distinguished in the progesterone receptor binding assay using cytosol from rabbit uterus homogenate and $^3$H-progesterone as reference substance by having a comparable or higher affinity for the progesterone receptor than drospirenone and by a smaller affinity for the mineralocorticoid receptor from rat kidney homogenate than drospirenone (see Tab. 1).

TABLE 1

| Example | PR [KF] | MR [KF] | PR [RBA] | MR [RBA] |
|---------|---------|---------|----------|----------|
| DRSP | 2.5 | 0.3 | 40 | 333 |
| 2 | 2.34 | 0.4 | 43 | 250 |
| 6 | 1.13 | 0.6 | 88 | 167 |
| 7 | 1.08 | 0.5 | 93 | 200 |
| 9 | 4.295 | 42 | 23 | 2 |
| 12 | 2.355 | 0.7 | 42 | 143 |
| 14 | 3.245 | 7.6 | 31 | 13 |
| 17 | 3.45 | 7.8 | 29 | 13 |
| 18 | 3.01 | 88 | 33 | 1 |

PR [KF]: $^3$H-progesterone = 1;
MR [KF]: $^3$H-aldosterone = 1;
PR [RBA]: $^3$H-progesterone = 100;
MR [RBA]: $^3$H-aldosterone = 100

The compounds of the invention are surprisingly distinguished by strong progestational activity and are highly effective after subcutaneous administration in the pregnancy maintenance test on rats.

Procedure for the Pregnancy Maintenance Test on Rats:

Removal of the corpora lutea or castration in pregnant rats induces abortion. Exogenous supply of progestins (progestogens) in combination with a suitable dose of an estrogen achieves maintenance of the pregnancy. The pregnancy maintenance test on ovariectomized rats serves to determine the peripheral progestational activity of a compound.

Rats are mated during proestrus overnight. The mating is checked on the morning of the following day by inspecting a vaginal smear. The presence of sperm is regarded in this case as day 1 of the onset of pregnancy. On day 8 of pregnancy, the animals are ovariectomized under ether anesthesia. Treatment with test compound and exogenous estrogen (esterone, 5 μg/kg/day) is carried out subcutaneously once a day from day 8 to day 15 or day 21 of pregnancy. The first administration on day 8 is carried out 2 hours before the castration. Intact control animals receive vehicle exclusively.

Evaluation:

At end of the experiment (day 15 or day 21), the animals are sacrificed under a $CO_2$ atmosphere and living fetuses (fetuses with beating heart) and implantation sites (early resorptions and dead fetuses including autolysis and atrophic placentae) in both uterine horns are counted. On day 22 it is additionally possible to examine fetuses for malformations. In uteri without fetuses or implantation sites, the number of nidation sites is found by staining with 10% strength ammonium sulfide solution. The pregnancy maintenance rate is calculated as the ratio of the number of living fetuses and the total number of nidation sites (both resorbed and dead fetuses, and nidation sites).

The compounds of the invention of the general formula I have very strong progestational activity with, at the same time, weak binding to the androgen receptor (dissociation).

It has additionally been found that compounds of the invention show a potassium-retaining, natriuretic (antimeralcorticoid) effect in adrenalectomized rats.

Owing to their progestational activity, the novel compounds of the general formula I can be used alone or in combination with estrogen in pharmaceutical products for contraception.

Because of their favorable profile of effects, the compounds of the invention are particularly suitable for the treatment of premenstrual symptoms such as headaches, depressive moods, water retention and mastodynia.

The dosage of the compounds of the invention in contraceptive products is to be from 0.01 to 5 mg, preferably 0.01 to 2 mg, per day.

The daily dose for the treatment of premenstrual symptoms is about 0.1 to 20 mg.

The progestational and estrogenic active ingredient components in contraceptive products are preferably administered orally together. The daily dose is preferably administered once a day.

Suitable estrogens are synthetic estrogens, preferably ethinylestradiol, but also mestranol.

The estrogen is administered in a daily amount which corresponds to from 0.01 to 0.04 mg of ethinyl-estradiol.

The novel compounds of the general formula I can also be employed in pharmaceutical products for the treatment of pre-, peri- and post-menopausal symptoms and in products for hormone replacement therapy (HRT).

Estrogens used in such products are primarily natural estrogens, especially estradiol or its esters, for example estradiol valerate or else conjugated estrogens (CEEs=conjugated equine estrogens) as are present for example in the product PREMARIN®.

Pharmaceutical products based on the novel compounds are formulated in a manner known per se by processing the active ingredient, where appropriate in combination with an estrogen, with the carrier substances, diluents, where appropriate masking flavors etc. usual in pharmaceutical technology, and converting into the desired administration form.

Suitable for the preferred oral administration are in particular tablets, coated tablets, capsules, pills, suspensions or solutions.

Particularly suitable for parenteral administration are oily solutions such as, for example, solutions in sesame oil, castor oil and cottonseed oil. To increase the solubility, it is possible to add solubilizers such as, for example, benzyl benzoate or benzyl alcohol.

It is also possible to incorporate the substances of the invention into a transdermal system and to use it for transdermal administration thereof.

The novel compounds of the general formula I are prepared according to the invention as described below. The synthetic route for the novel 19-nor-20-spiroxenones shown in scheme 1 starts for example from dienol ether 2 (Hofmeister et al. *Arzneim.-Forsch.* 36(1), 781, 1986).

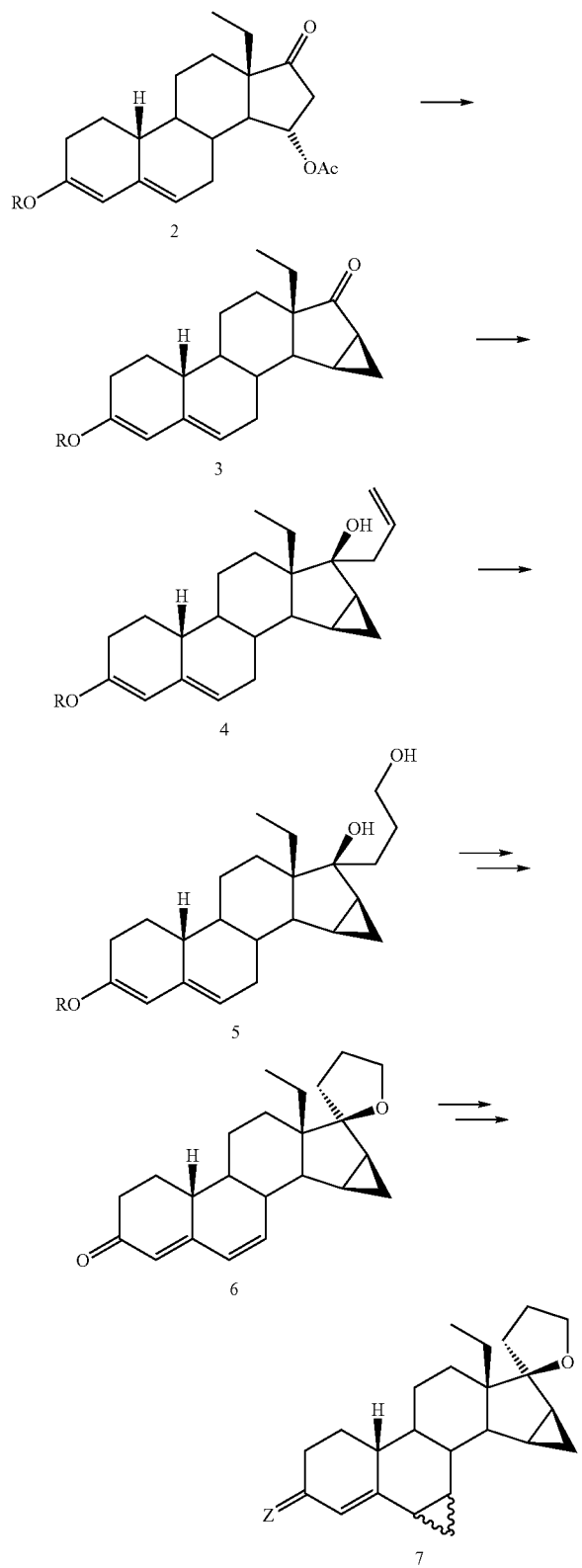

Compound 3 (R=methyl) is then prepared by methenylation of the 15-acetate 2 by known methods, for example with dimethylsulfoxonium methylide and sodium hydroxide (see, for example, DE-A 11 83 500, DE-A 29 22 500, EP-A 0 019 690, U.S. Pat. No. 4,291,029; E. J. Corey and M. Chaykovsky, *J. Am. Chem. Soc.* 84, 867 (1962)).

Allylation is then carried out in position 17, for example with allylmagnesium bromide in diethyl ether to give a compound 4. Hydroboronation for example with 9-borabicyclo [3.3.1]nonane and oxidative working up for example with hydrogen peroxide results in the primary alcohol 5.

Introduction of a $\Delta^6$ double bond takes place by bromination of the 3,5-dienol ether 5 and subsequent elimination of hydrogen bromide (see, for example, J. Fried, J. A. Edwards, *Organic Reactions in Steroid Chemistry*, van Nostrand Reinhold Company 1972, pp. 265-374).

The dienol ether bromination can take place for example in analogy to the method of J. A. Zderic, Humberto Carpio, A. Bowers and Carl Djerassi in *Steriods* 1, 233 (1963). The elimination of hydrogen bromide takes place by heating the 6-bromo compound with basic reagents such as, for example, LiBr or $Li_2CO_3$ in aprotic solvents such as dimethylformamide at temperatures of 50-120° C. or else by heating the 6-bromo compounds in a solvent such as collidine or lutidine, to give compound 6. Compound 6 is then converted by methenylation of the $\Delta^6$ double bond by known methods, e.g. with dimethyl-sulfoxonium methylide (see, for example, DE-A 11 83 500, DE-A 29 22 500, EP-A 0 019 690, U.S. Pat. No. 4,291,029; E. J. Corey and M. Chaykovsky, *J. Am. Chem. Soc.* 84, 867 (1962)) into a compound 7, resulting in a mixture of the $\alpha$ and $\beta$ isomers (compounds 3a/3b) which can be separated into the individual isomers for example by chromatography.

Introduction of a substituent $R^4$ can for example starting from a compound of the formula 6 by epoxidation of the $\Delta^4$ double bond with hydrogen peroxide under alkaline conditions and reaction of the resulting epoxides in a suitable solvent treated with acids of the general formula H—$R^4$, where —$R^4$ may be a halogen atom or a pseudohalogen, or reacted with catalytic amounts of mineral acid and, where appropriate, the resulting 4-bromo compounds of the general formula I (where $R^4$=bromine) reacted with methyl 2,2-difluoro-2-(fluorosulfonyl)acetate in dimethylformamide in the presence of copper(I) iodide.

Introduction of a 6-methylene group can take place for example starting from a 3-amino 3,5-diene derivative by reaction with formalin in alcoholic solution to form a 6α-hydroxymethyl group and subsequent acidic elimination of water, for example with hydrochloric acid in dioxane/water. The elimination of water can, however, also take place in such a way that initially the hydroxy group is replaced by a better leaving group and is then eliminated. Examples of suitable leaving groups are the mesylate, tosylate or benzoate (see DE-A 34 02 3291, EP-A 0 150 157, U.S. Pat. No. 4,584,288; K. Nickisch et al., *J. Med. Chem.* 34, 2464 (1991)).

A further possibility for preparing the 6-methylene compounds consists of direct reaction of the 4(5) unsaturated 3-ketones with acetals of formaldehyde in the presence of sodium acetate with, for example, phosphorus oxychloride or phosphorus pentachloride in suitable solvents such as chloroform (see, for example, K. Annen, H. Hofmeister, H. Laurent and R. Wiechert, *Synthesis* 34 (1982)).

The 6-methylene compounds can be used to prepare compounds of the general formula I in which $R^6$ is equal to methyl, and $R^6$ and $R^7$ together form an additional bond.

For this purpose it is possible to use for example a method described by D. Burn et al. in *Tetrahedron* 21, 1619 (1965), in which isomerization of the double bond is achieved by heating the 6-methylene compounds in ethanol with 5% palladium-carbon catalyst, which has been pretreated either with hydrogen or by heating with a small amount of cyclohexene. The isomerization can also take place with a non-pretreated catalyst if a small amount of cyclohexene is added to the reaction mixture. The appearance of small proportions of hydrogenated products can be prevented by adding an excess of sodium acetate.

Preparation of 6-methyl-4,6-dien-3-one derivatives is, however, also possible directly (see K. Annen, H. Hofmeister, H. Laurent and R. Wiechert, *Lieb. Ann.* 712 (1983)).

Compounds in which $R^6$ is an α-methyl function can be prepared from the 6-methylene compounds by hydrogenation under suitable conditions. The best results (selective hydrogenation of the exo-methylene function) are achieved by transfer hydrogenation (E. A. Brande, R. P. Linstead and P. W. D. Mitchell, *J. Chem. Soc.* 3578 (1954)). Heating the 6-methylene derivatives in a suitable solvent such as, for example, ethanol, in the presence of a hydride donor such as, for example, cyclohexene, results in very good yields of 6α-methyl derivatives. Small proportions of 6β-methyl compound can be isomerized with acid (see, for example, D. Burn, D. N. Kirk and V. Petrow, *Tetrahedron* 1619 (1965)).

Targeted preparation of 6β-alkyl compounds is also possible. For this purpose, the 4(5)-unsaturated 3-ketones are reacted for example with ethylene glycol, trimethyl orthoformate in dichloromethane in the presence of catalytic amounts of an acid (e.g. p-toluenesulfonic acid) to give the corresponding 3-ketals. The double bond in the 5(6) position isomerizes during this ketalization. Selective epoxidation of this 5(6) double bond takes place for example by using organic peracids, e.g. m-chloro-perbenzoic acid, in suitable solvents such as dichloromethane. As an alternative to this, the epoxidation can also take place with hydrogen peroxide in the presence of, for example, hexachloroacetone or 3-nitrotrifluoroacetophenone. The 5α,6α-epoxides formed can then be opened axially using appropriate alkylmagnesium halides or alkyllithium compounds. 5α-hydroxy-6β-alkyl compounds are obtained in this way. Cleavage of the 3-keto protective group can take place to obtain the 5α-hydroxy function by treatment under mild acidic conditions (acetic acid or 4N hydrochloric acid at 0° C.). Basic elimination of the 5α-hydroxy function with, for example, dilute aqueous sodium hydroxide solution affords the 3-keto 4-ene compounds with a 6-alkyl group in the β configuration. As an alternative to this, ketal cleavage under more drastic conditions (aqueous hydrochloric acid or another strong acid) affords the corresponding 6a-alkyl compounds.

Compounds substituted in position 7 by an alkyl, alkenyl or cycloalkyl group can be obtained as described in the examples or in analogy to these methods using reagents analogous to those described therein.

The resulting compounds of the general formula I in which Z is an oxygen atom can if desired be converted by reaction with hydroxylamine hydrochloride in the presence of a tertiary amine at temperatures between −20 and +40° C. into their corresponding oximes (general formula I with Z meaning =NOH, where the hydroxy group may be synthetic or anti). Suitable tertiary bases are for example trimethylamine, triethylamine, pyridine, N,N-dimethylaminopyridine, 1,5-diazabicyclo[4.3.0]non-5-ene (DBN) and 1,5-diazabicyclo [5.4.0]undec-5-ene (DBU), with preference for pyridine. This proceeds in analogy to the description in WO 98/24801 for the preparation of corresponding 3-oxyimino derivatives of drospirenone.

Removal of the 3-oxo group to prepare a final product of the general formula I with Z meaning two hydrogen atoms can take place for example by the method indicated in DE-A 28 05 490 by reductive cleavage of a thioketal of the 3-keto compound.

The following examples serve to explain the invention in more detail:

EXAMPLE 1

18-Methyl-15β,16β-methylene-19-nor-20-spiroxa-4, 6-dien-3-one a) 3-Methoxy-18-methyl-15β,16β-methylene-estra-3,5-dien-17-one A suspension of 92.0 g of 15α-acetoxy-3-methoxy-18-methylestra-3,5-dien-17-one (Hofmeister et al. Arzneim.-Forsch. 36(1), 781, 1986) in 500 ml of dimethyl sulfoxide was added to a suspension of 254 g of trimethylsulfoxonium iodide in 1165 ml of dimethyl sulfoxide which had previously been stirred with 43.5 g of sodium hydroxide at room temperature under argon for 2 hours. The latter was stirred at room temperature for a further 1.5 hours. This was followed by stirring into 15 l of ice-water/sodium chloride, and the precipitate was filtered off, washed with water, and dried in vacuo at 60° C. 94.5 g of 3-methoxy-18-methyl-15β,16β-methylene-estra-3,5-dien-3-one were obtained as crude product. 134-135° C., $[\alpha]_D$ −215.2° (chloroform, c=9.9 mg/ml)

b) 3-Methoxy-18-methyl-15β,16β-methylene-17α-(prop-2-enyl)-estra-3,5-dien-17β-ol 574 ml of a 1M solution of allylmagnesium bromide in diethyl ether were added to a solution 75.8 g of 3-methoxy-18-methyl-15β,16β-methylene-estra-3,5-dien-17-one in 920 ml of dichloromethane at 0° C. and stirred at 0° C. under argon for 1 hour. This was followed by dropwise addition of 290 ml of a saturated ammonium chloride solution at 0° C., stirring at 0° C. for 0.5 hours, addition to water, taking up in ethyl acetate, washing with water until neutral, drying over sodium sulfate, and concentrating in vacuo. 86.5 g of 3-methoxy-18-methyl-15β,16β-methylene-17α-(prop-2-enyl)-estra-3,5-dien-17β-ol were obtained as crude product. Crystals of the pure compound had a melting point of 110-112° C., $[\alpha]_D$=−80.2° (chloroform, c=9.94 mg/ml).

c) 17α-(3-Hydroxypropanyl)-3-methoxy-18-methyl-15β,16β-methylene-estra-3,5-dien-17β-ol 1.5 l of a 0.5M solution of 9-borabicyclo[3.3.1]nonane in tetrahydrofuran were added to a solution of 86.5 g of 3-methoxy-18-methyl-15β,16β-methylene-17α-(prop-2-enyl)estra-3,5-dien-17β-ol in 1 l of tetrahydrofuran at 25° C., and the mixture was stirred at 25° C. under argon for 4 hours and then, at 0° C., 33.77 g of sodium hydroxide in 475 ml of water were slowly added dropwise and, after stirring at 25° C. for 5 minutes, 172 ml of 30% strength hydrogen peroxide were slowly added dropwise and stirred at 25° C. for 18 hours. This was followed by stirring into ice-water/sodium chloride, removal of the precipitate by filtration, washing with water and drying to dryness in vacuo at 60° C. 91.5 g of 17α-(3-hydroxypropanyl)-3-methoxy-18-methyl-15β,16β-methylene-estra-3,5-dien-17β-ol were obtained as crude product. Crystals of the pure compound had a melting point of 152-154° C., $[\alpha]_D$=−155.2° (chloroform, c=9.76 mg/ml).

d) 17β-Hydroxy-17α-(3-hydroxypropanyl)-18-methyl-15β,16β-methylene-estra-4,6-dien-3-one To a suspension of 91.5 g of 17α-(3-hydroxypropanyl)-3-methoxy-18-methyl-15β,16β-methylene-estra-3,5-dien-17β-ol in 915 ml of 1-methyl-2-pyrrolidone were successively added, at 0° C., 91.5 ml of a 10% strength sodium acetate solution and, at this temperature, 35.9 g of 1,3-dibromo-5,5-dimethylhydantoin in portions, the mixture was stirred at 0° C. (ice bath) for 0.5 hour, 34 g of lithium bromide and 29.9 g of lithium carbonate were added, and the mixture was stirred at a bath temperature of 100° C. for 3.5 hours. It was then stirred into ice-water/sodium chloride, and the precipitate was removed by filtration, washed with water and stirred in the moist state with 250 ml of ethyl acetate. 44.1 g of 17β-hydroxy-17α-(3-hydroxypropanyl)-18-methyl-15β,16β-methylene-estra-4,6-dien-3-one were obtained as crystals of melting point 132-135° C., $[\alpha]_D$=−14.0° (pyridine, c=4.28 mg/ml).

e) 18-Methyl-15β,16β-methylene-19-nor-20-spiroxa-4,6-dien-3-one 720 mg of p-toluenesulfonyl chloride are added to a solution of 1.07 g of 17β-hydroxy-17α-(3-hydroxy-propanyl)-18-methyl-15β,16β-methylene-estra-4,6-dien-3-one in 2.5 ml of pyridine, and the mixtures is stirred at room temperature for 18 hours. It was then added to water and extracted three times with ethyl acetate, and the combined organic phases were washed with 1M hydrochloric acid, water and brine until neutral, dried over sodium sulfate, concentrated in vacuo and chromatographed on silica gel with hexane/ethyl acetate. 630 mg of pure 18-methyl-15β,16β-methylene-19-nor-20-spiroxa-4,6-dien-3-one were obtained. Crystal-lization from acetone/hexane resulted in crystals of melting point 134-135° C., $[\alpha]_D$=−80.6° C. (chloroform, c=10.03 mg/ml).

EXAMPLE 2

18-Methyl-6α,7α,15β,16β-dimethylene-19-nor-20-spirox-4-en-3-one

A suspension of 9.41 g of trimethylsulfoxonium iodide in 210 ml of dimethyl sulfoxide was stirred with 1.71 g of sodium hydride (60% in oil) at room temperature under argon for 2 hours and, after addition of 5.7 g of 18-methyl-15β,16β-methylene-19-nor-20-spiroxa-4,6-dien-3-one (example 1), and stirred at room temperature for 20 hours. Working up included addition to water, extraction three times with ethyl acetate, washing with water and brine until neutral, drying over sodium sulfate, evaporating to dryness in vacuo and chromatography on silica gel with dichloromethane/-acetone. Fraction II of the chromatography afforded 438 mg of 18-methyl-6α,7α,15β,16β-dimethylene-19-nor-20-spirox-4-en-3-one. Crystallization from acetone resulted in crystals of melting point 228-230° C., $[\alpha]_D$=+40.2°+/−0.2° (chloroform, c=11.1 mg/ml)

EXAMPLE 3

18-Methyl-6β,7β,15β,16β-dimethylene-19-nor-20-spirox-4-en-3-one

By the method of example 2, fraction I of the chromatography afforded 1.2 g of 18-methyl-6β,7β,15β,16β-dimethylene-19-nor-20-spirox-4-en-3-one. Crystallization from acetone/hexane resulted in crystals of melting point 154-155° C., $[\alpha]_D$=−175.1° (chloroform, c=9.5 mg/ml).

EXAMPLE 4

18-Methyl-15β,16β-methylene-7α-propyl-19-nor-20-spirox-4-en-3-one 31.2 mg of copper(I) chloride were added to a solution of 1.0 g of 18-methyl-15β,16β-methylene-19-nor-20-spiroxa-4,6-dien-3-one (example 1) in 20 ml of tetrahydrofuran at room temperature, and the mixture was stirred for 10 minutes before being cooled to −15° C., having 200 mg of aluminium chloride added, being stirred at this temperature for 30 minutes, having 3.34 ml of propylmagnesium bromide solution (2M in tetrahydrofuran) added dropwise, and being stirred at −15° C. for one hour. Working up involved adding 3 ml of 2M hydrochloric acid to the reaction mixture at −15° C., stirring at room temperature for 0.5 hours, adding to water, extracting three times with ethyl acetate, drying over sodium sulfate, concentrating in vacuo, and chromatography on silica gel with hexane/ethyl acetate. Crystallization of fraction I resulted in 233 mg of 18-methyl-15β,16β-methylene-7β-propyl-19-nor-20-spirox-4-en-3-one as crystals of melting point 142-143° C., $[\alpha]_D$=−2.7° (chloroform, c=9.5 mg/ml).

EXAMPLE 5

18-Methyl-15β,16β-methylene-7β-propyl-19-nor-20-spirox-4-en-3-one

By the method of example 4, fraction II of the chromatography afforded 241 mg of 18-methyl-15β,16β-methylene-7β-propyl-19-nor-20-spirox-4-en-3-one as solid of melting point 87-88° C., $[\alpha]_D$=−10.8° (chloroform, c=10.0 mg/ml)

EXAMPLE 6

7α,18-Dimethyl-15β,16β-methylene-19-nor-20-spirox-4-en-3-one

By the method of example 4 with 3M methylmagnesium bromide in ether instead of propylmagnesium bromide, fraction I of the chromatography afforded 483 mg of 7α,18-dimethyl-15β,16β-methylene-19-nor-20-spirox-4-en-3-one as solid of melting point 190-191° C., $[\alpha]_D$=6.5° (chloroform, c=10.16 mg/ml).

EXAMPLE 7

7β,18-Dimethyl-15β,16β-methylene-19-nor-20-spirox-4-en-3-one

By the method of example 6, fraction II of the chromatography afforded 201 mg of 7β,18-dimethyl-15β,16β-methylene-19-nor-20-spirox-4-en-3-one as solid of melting point 172-173° C., $[\alpha]_D$=−11.2° (chloroform, c=10.35 mg/ml).

EXAMPLE 8

7α-Ethyl-18-methyl-15β,16β-methylene-19-nor-20-spirox-4-en-3-one

By the method of example 4 with 3M ethylmagnesium bromide in ether instead of propylmagnesium bromide, fraction I of the chromatography afforded 453 mg of 7α-ethyl-18-methyl-15β,16β-methylene-19-nor-20-spirox-4-en-3-one as solid of melting point 197-198° C., $[\alpha]_D$=−6.7° (chloroform, c=10.42 mg/ml).

EXAMPLE 9

7β-Ethyl-18-methyl-15β,16β-methylene-19-nor-20-spirox-4-en-3-one

By the method of example 8, fraction II of the chromatography afforded 113 mg of 7β-ethyl-18-methyl-15β,16β-methylene-19-nor-20-spirox-4-en-3-one as solid of melting point 185-187° C., $[\alpha]_D$=−11.7° (chloroform, c=9.4 mg/ml).

EXAMPLE 10

7α-Ethenyl-18-methyl-15β,16β-methylene-19-nor-20-spirox-4-en-3-one

By the method of example 4, fraction I of the chromatography afforded 280.6 mg of 7α-ethenyl-18-methyl-15β,16β-methylene-19-nor-20-spirox-4-en-3-one as solid of melting point 188-190° C., $[\alpha]_D$=−59.8° (chloroform, c=9.87 mg/ml).

EXAMPLE 11

7β-Ethenyl-18-methyl-15β,16β-methylene-19-nor-20-spirox-4-en-3-one

By the method of example 4, fraction II of the chromatography afforded 54.4 mg of 7β-Ethenyl-18-methyl-15β,16β-methylene-19-nor-20-spirox-4-en-3-one as solid of melting point 149-150° C. $[\alpha]_D$=−37.6° (chloroform, c=5.11 mg/ml).

EXAMPLE 12

7α-Cyclopropyl-18-methyl-15β,16β-methylene-19-nor-20-spirox-4-en-3-one

By the method of example 4, fraction I of the chromatography afforded 360 mg of 7α-cyclopropyl-18-methyl-15β,16β-methylene-19-nor-20-spirox-4-en-3-one as solid of melting point 167-168° C. $[\alpha]_D$=−55.3° (chloroform, c=10.14 mg/ml).

EXAMPLE 13

7β-Cyclopropyl-18-methyl-15β,16β-methylene-19-nor-20-spirox-4-en-3-one

By the method of example 4, fraction II of the chromatography afforded 63 mg of 7β-cyclopropyl-18-methyl-15β,16β-methylene-19-nor-20-spirox-4-en-3-one as solid of melting point 124-126° C. $[\alpha]_D$=−16.9° (chloroform, c=10.18 mg/ml).

EXAMPLE 14

4,18-Dimethyl-15β,16β-methylene-19-nor-20-spirox-4-en-3-one a) 15α-Acetoxy-3,3-ethylenedioxy-18-methyl-19-nor-androst-5-en-17-one 40 ml of ethylene glycol and 27.5 ml of trimethyl orthoformate were added to a solution of 10 g of 15α-acetoxy-3-methoxy-18-methyl-estra-3,5-dien-17-one in 140 ml of dichloromethane and, after addition of 670 mg of para-toluenesulfonic acid, the mixture was stirred at room temperature for 1 hour. This was followed by addition of 1.85 ml of pyridine, dilution with dichloromethane, washing with saturated sodium bicarbonate solution, water and brine, drying over sodium sulfate and concentrating in vacuo. 11.1 g of crude 15α-acetoxy-3,3-ethylenedioxy-18-methyl-19-nor-androst-5-en-17-one were obtained.

b) 3,3-Ethylenedioxy-18-methyl-15β,16β-methylene-19-nor-androst-5-en-17-one

A suspension of 28.75 g of trimethylsulfoxonium iodide in 210 ml of dimethyl sulfoxide was stirred with 4.92 g of sodium hydride (60% in oil) at room temperature under argon for 2 hours and, after addition of 11.1 g of 15α-acetoxy-3,3-ethylenedioxy-18-methyl-19-nor-androst-5-en-17-one, stirred at room temperature for 20 hours. Working up involved addition to water, extraction three times with ethyl acetate, washing with water and brine until neutral, drying over sodium sulfate and concentrating to dryness in vacuo. 10.2 g of crude 3,3-ethylenedioxy-18-methyl-15β,16β-methylene-19-nor-androst-5-en-17-one were obtained. Crystallization from acetone resulted in crystals of melting point 221.7° C.

c) 3,3-Ethylenedioxy-18-methyl-15β,16β-methylene-17α-(prop-2-enyl)-19-nor-androst-5-en-17β-ol 71 ml of a 1M allylmagnesium bromide solution in diethyl ether were added slowly to a solution of 10.2 g of 3,3-ethylenedioxy-18-methyl-15β,16β-methylene-19-nor-androst-5-en-17-one in 120 ml of dichloromethane at 0° C., and the mixture was stirred at 0° C. for one hour. This was followed by dropwise addition of 40 ml of a saturated ammonium chloride solution, stirring at 0° C. for 0.5 hours, addition to water, extraction with ethyl acetate, washing with water and brine until neutral, drying over sodium sulfate and concentrating to dryness in vacuo. Chromatography on silica gel with hexane/ethyl acetate afforded 7.33 g of pure 3,3-ethylenedioxy-18-methyl-15β,16β-methylene-17α-(prop-2-enyl)-19-nor-androst-5-en-17β-ol d) 3,3-Ethylenedioxy-17α-(3-hydroxypropyl)-18-methyl-15β,16β-methylene-19-nor-androst-5-en-17β-ol 1.4 l of a 0.5M solution of 9-borabicyclo[3.3.1]nonane solution in tetrahydrofuran were added to a solution of 80.3 g of 3,3-ethylenedioxy-18-methyl-15β,16β-methylene-17α-(prop-2-enyl)-19-nor-androst-5-en-17β-ol in 900 ml of tetrahydrofuran at 25° C., and the mixture was stirred at 25° C. under argon for 4 hours followed by slow dropwise addition of 30.5 g of sodium hydroxide in 425 ml of water at 0° C., stirring at 25° C. for 5 minutes, slow dropwise addition of 155 ml of 30% strength hydrogen peroxide, and stirring at 25° C. for 18 hours. This was followed by dilution with ethyl acetate, washing with water, drying over sodium sulfate and concentrating to dryness in vacuo at 60° C. 80.7 g of 3,3-ethylenedioxy-17α-(3-hydroxypropyl)-18-methyl-15β,16β-methylene-19-nor-androst-5-en-17β-ol were obtained as an oil.

e) 3,3-Ethylenedioxy-18-methyl-15β,16β-methylene-19-nor-20-spirox-5-ene

A solution of 80.7 g of 3,3-ethylenedioxy-17α-(3-hydroxypropyl)-18-methyl-15β,16β-methylene-19-nor-androst-5-en-17β-ol in 170 ml of pyridine was mixed with 48 g of para-toluenesulfonyl chloride and stirred at 25° C. for 24 hours. It was then diluted with ethyl acetate, washed with water and saturated brine until neutral, dried over sodium sulfate and concentrated to dryness in vacuo at 60° C. 75.8 g of crude product were obtained. Chromatography on silica gel with hexane/ethyl acetate afforded 50.5 g of pure 3,3-ethylenedioxy-18-methyl-15β,16β-methylene-19-nor-20-spirox-5-ene. Crystals of the pure compound had a melting point of 58-60° C., $[\alpha]_D=-9.3°$ (chloroform, c=10.59 mg/ml).

f) 18-Methyl-15β,16β-methylene-19-nor-20-spirox-4-en-3-one 50 ml of aqueous sulfuric acid (81 strength) were added to a solution of 50.5 g of 3,3-ethylenedioxy-18-methyl-15β,16β-methylene-19-nor-20-spirox-5-ene in 500 ml of methanol, and the mixture was stirred at 25° C. for 8.5 hours. This was followed by addition to sodium bicarbonate solution, extraction three times with ethyl acetate, washing with water until neutral, drying over sodium sulfate and concentration to dryness in vacuo at 50° C. 46.2 g of crude product were obtained. Chromatography on silica gel with dichloromethane/-acetone resulted in 25.8 g of pure 18-methyl-15β,16β-methylene-19-nor-20-spirox-4-en-3-one. Crystals of the pure compound had a melting point of 208-210° C., $[\alpha]_D=+4.4°$ (chloroform, c=10.1 mg/ml).

g) 4,18-Dimethyl-15β,16β-methylene-19-nor-20-spirox-4-en-3-one

To a solution of 508 mg of potassium tert-butoxide in 20 ml of tert-butanol were added, at a bath temperature of 100° C., a solution of 1 g of 18-methyl-15β,16β-methylene-19-nor-20-spirox-4-en-3-one in 20 ml of tert-butanol and, over the course of 4 hours, a second solution of 1.46 ml of iodomethane in 50 ml of tert-butanol, and the mixture was stirred at a bath temperature of 100° C. for another hour. It was then concentrated in vacuo to one third the volume, diluted with ethyl acetate, washed twice with water and three times with saturated brine, dried over sodium sulfate and concentrated to dryness in vacuo. 1.1 g of crude product were obtained. Chromatography on silica gel with hexane/ethyl acetate afforded 301.2 mg of 4,18-dimethyl-15β,16β-methylene-19-nor-20-spirox-4-en-3-one as solid of melting point 155-156° C. $[\alpha]_D=+1°$ (chloroform, c=10.75 mg/ml).

EXAMPLE 15

4-Chloro-18-methyl-15β,16β-methylene-19-nor-20-spirox-4-en-3-one 0.38 ml of sulfuryl chloride was added to a solution of 1 g of 18-methyl-15β,16β-methylene-19-nor-20-spirox-4-en-3-one in 10 ml of pyridine at a bath temperature of 0° C., and stirring was continued for 3 hours. This was followed by addition to water, extraction three times with ethyl acetate, washing with water until neutral, drying over sodium sulfate and concentration to dryness in vacuo. 1.2 g of crude product were obtained. Chromatography on silica gel with hexane/ethyl acetate afforded 604.8 mg of pure 4-chloro-18-methyl-15β,16β-methylene-19-nor-20-spirox-4-en-3-one as solid of melting point 149-151° C. $[\alpha]_D=+9.4°$ (chloroform, c=11.06 mg/ml).

EXAMPLE 16

4,18-Dimethyl-6α,7α,15β,16β-dimethylene-19-nor-20-spirox-4-en-3-one

The method of example 14 with 0.5 g of 18-methyl-6α,7α,15β,16β-dimethylene-19-nor-20-spirox-4-en-3-one resulted in 220 mg of 4,18-dimethyl-6α,7α,15β,16β-dimethylene-19-nor-20-spirox-4-en-3-one as solid of melting point 190-191° C. $[\alpha]_D=+103.3°$ (chloroform, c=10.22 mg/ml).

EXAMPLE 17

4,18-Dimethyl-6β,7β,15β,16β-dimethylene-19-nor-20-spirox-4-en-3-one

The method of example 14 with 0.66 g of 18-methyl-6β,7β,15β,16β-dimethylene-19-nor-20-spirox-4-en-3-one resulted in 186.7 mg of 4,18-dimethyl-6β,7β,15β,16β-dimethylene-19-nor-20-spirox-4-en-3-one as solid of melting point 175-177° C. $[\alpha]_D=-230.7°$ (chloroform, c=10.79 mg/ml).

EXAMPLE 18

4-Chloro-18-methyl-6β,7β,15β,16β-dimethylene-19-nor-20-spirox-4-en-3-one

The method of example 15 with 0.66 g of 18-methyl-6β,7β,15β,16β-dimethylene-19-nor-20-spirox-4-en-3-one resulted in 303.4 mg of 4-chloro-18-methyl-6β,7β,15β,16β-dimethylene-19-nor-20-spirox-4-en-3-one as solid of melting point 152-153° C. $[\alpha]_D=-222.7°$ (chloroform, c=10.30 mg/ml).

EXAMPLE 19

4-Chloro-18-methyl-6α,7α,15β,16β-dimethylene-19-nor-20-spirox-4-en-3-one

The method of example 15 with 534 mg of 18-methyl-6α,7α,15β,16β-dimethylene-19-nor-20-spirox-4-en-3-one resulted in 128 mg of 4-chloro-18-methyl-6α,7α,15β,16β-dimethylene-19-nor-20-spirox-4-en-3-one as solid of melting point 177-178° C. $[\alpha]_D=+80.0°$ (chloroform, c=9.94 mg/ml).

The invention claimed is:
1. An 18-Methyl-15β,16β-methylene-19-nor-20-spirox-4-en-3-one of formula I

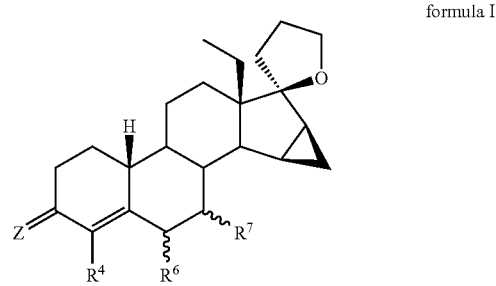

formula I in which
Z is an oxygen atom, two hydrogen atoms, a group =NOR or =NNHSO$_2$R,
R is a hydrogen atom or a straight- or branched-chain alkyl group having 1 to 4 carbon atoms,
R$^4$ is a hydrogen atom, a halogen atom or a trifluoromethyl group, and
R$^6$ and/or R$^7$ may have α or β configuration, and
R$^6$ and R$^7$ are independently of one another a hydrogen atom or a straight- or branched-chain alkyl group having 1 to 4 carbon atoms or a straight- or branched-chain alkenyl group having 2 to 4 carbon atoms or a saturated cycloalkyl group having 3 to 5 carbon atoms or together are a methylene group or a double bond.

2. A compound of claim 1, which is
18-methyl-15β,16β-methylene-19-nor-20-spiroxa-4,6-dien-3-one,
18-methyl-15β,16β-methylene-19-nor-20-spirox-4-en-3-one,
18-methyl-6β,7β,15β,16β-dimethylene-19-nor-20-spirox-4-en-3-one,
18-methyl-6α,7α,15β,16β-dimethylene-19-nor-20-spirox-4-en-3-one,
18-methyl-15β,16β-methylene-7α-propyl-19-nor-20-spirox-4-en-3-one,
18-methyl-15β,16β-methylene-7β-propyl-19-nor-20-spirox-4-en-3-one,
7α,18-dimethyl-15β,16β-methylene-19-nor-20-spirox-4-en-3-one,
7β,18-dimethyl-15β,16β-methylene-19-nor-20-spirox-4-en-3-one,
7α-ethyl-18-methyl-15β,16β-methylene-19-nor-20-spirox-4-en-3-one,
7β-ethyl-18-methyl-15β,16β-methylene-19-nor-20-spirox-4-en-3-one,
7α-ethenyl-18-methyl-15β,16β-methylene-19-nor-20-spirox-4-en-3-one,
7β-ethenyl-18-methyl-15β,16β-methylene-19-nor-20-spirox-4-en-3-one,
7α-cyclopropyl-18-methyl-15β,16β-methylene-19-nor-20-spirox-4-en-3-one,
7β-cyclopropyl-18-methyl-15β,16β-methylene-19-nor-20-spirox-4-en-3-one,
4,18-dimethyl-15β,16β-methylene-19-nor-20-spirox-4-en-3-one,
4-chloro-18-methyl-15β,16β-methylene-19-nor-20-spirox-4-en-3-one,
4,18-dimethyl-6β,7β,15β,16β-dimethylene-19-nor-20-spirox-4-en-3-one,
4,18-dimethyl-6α,7α,15β,16β-dimethylene-19-nor-20-spirox-4-en-3-one,
4-chloro-18-methyl-6β,7β,15β,16β-dimethylene-19-nor-20-spirox-4-en-3-one, or
4-chloro-18-methyl-6α,7α,15β,16β-dimethylene-19-nor-20-spirox-4-en-3-one.

3. A pharmaceutical product comprising at least one compound as claimed in claim 1 and a pharmaceutically acceptable carrier.

4. The pharmaceutical product as claimed in claim 3, additionally comprising at least one estrogen.

5. The pharmaceutical product as claimed in claim 4 comprising ethinylestradiol.

6. The pharmaceutical product as claimed in claim 4, comprising a natural estrogen.

7. The pharmaceutical product as claimed in claim 6, comprising estradiol.

8. The pharmaceutical product as claimed in claim 6, comprising estradiol valerate.

9. The pharmaceutical product as claimed in claim 6, comprising at least one conjugated estrogen.

10. A pharmaceutical product comprising at least one compound as claimed in claim 2 and a pharmaceutically acceptable carrier.

11. The pharmaceutical product as claimed in claim 10, additionally comprising at least one estrogen.

12. A compound of claim 1, wherein R is a hydrogen atom or a straight- or branched-chain alkyl group having 3 to 4 carbon atoms.

13. A compound of claim 1, wherein $R^6$ and $R^7$ are independently of one another a hydrogen atom or a straight- or branched-chain alkyl group having 3 to 4 carbon atoms or a straight- or branched-chain alkenyl group having 3 to 4 carbon atoms or a saturated cycloalkyl group having 3 to 5 carbon atoms or together are a methylene group or a double bond.

14. A compound of claim 12, wherein $R^6$ and $R^7$ are independently of one another a hydrogen atom or a straight- or branched-chain alkyl group having 3 to 4 carbon atoms or a straight- or branched-chain alkenyl group having 3 to 4 carbon atoms or a saturated cycloalkyl group having 3 to 5 carbon atoms or together are a methylene group or a double bond.

15. An 18-Methyl-15β,16β-methylene-19-nor-20-spirox-4-en-3-one of formula I

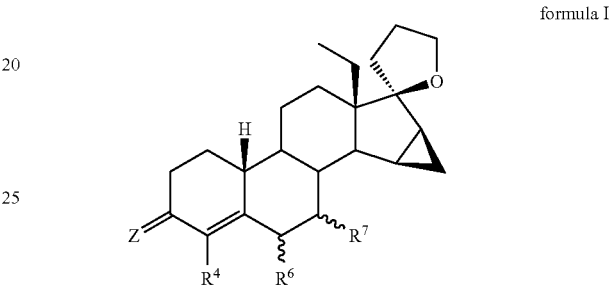

formula I in which
Z is an oxygen atom,
R is a hydrogen atom or a straight- or branched-chain alkyl group having 1 to 4 carbon atoms,
$R^4$ is a hydrogen atom, a halogen atom or a trifluoromethyl group, and
$R^6$ and/or $R^7$ may have α or β configuration, and
$R^6$ and $R^7$ are independently of one another a hydrogen atom or a straight- or branched-chain alkyl group having 1 to 4 carbon atoms or a straight- or branched-chain alkenyl group having 2 to 4 carbon atoms or a saturated cycloalkyl group having 3 to 5 carbon atoms or together are a methylene group or a double bond.

16. A compound of claim 15, wherein R is a hydrogen atom or a straight- or branched-chain alkyl group having 3 to 4 carbon atoms.

17. A compound of claim 15, wherein $R^6$ and $R^7$ are independently of one another a hydrogen atom or a straight- or branched-chain alkyl group having 3 to 4 carbon atoms or a straight- or branched-chain alkenyl group having 3 to 4 carbon atoms or a saturated cycloalkyl group having 3 to 5 carbon atoms or together are a methylene group or a double bond.

18. A compound of claim 16, wherein $R^6$ and $R^7$ are independently of one another a hydrogen atom or a straight- or branched-chain alkyl group having 3 to 4 carbon atoms or a straight- or branched-chain alkenyl group having 3 to 4 carbon atoms or a saturated cycloalkyl group having 3 to 5 carbon atoms or together are a methylene group or a double bond.

19. A pharmaceutical product comprising at least one compound as claimed in claim 15 and a pharmaceutically acceptable carrier.

20. The pharmaceutical product as claimed in claim 19, additionally comprising at least one estrogen.

* * * * *